United States Patent

Horzewski et al.

[11] Patent Number: 5,470,322
[45] Date of Patent: Nov. 28, 1995

[54] REINFORCED MULTILUMEN CATHETER FOR AXIALLY VARYING STIFNESS

[75] Inventors: Michael J. Horzewski; Nitin P. Matani, both of San Jose, Calif.

[73] Assignee: Danforth Biomedical Inc., Santa Clara, Calif.

[21] Appl. No.: 227,954

[22] Filed: Apr. 15, 1994

[51] Int. Cl.⁶ .................................................. A61M 25/00
[52] U.S. Cl. ........................................... 604/280; 604/282
[58] Field of Search ..................... 604/96–103, 43–45, 604/280, 282; 606/192, 194

[56] References Cited

U.S. PATENT DOCUMENTS

| | | |
|---|---|---|
| 4,248,234 | 2/1981 | Assenza et al. . |
| 4,662,404 | 5/1987 | LeVeen et al. . |
| 4,771,777 | 9/1988 | Horzewski et al. ............... 606/194 |
| 4,775,371 | 10/1988 | Mueller, Jr. . |
| 4,842,590 | 6/1989 | Tanabe et al. . |
| 4,899,787 | 2/1990 | Ouchi et al. ..................... 138/131 |
| 4,960,410 | 10/1990 | Pinchuk . |
| 4,976,690 | 12/1990 | Solar et al. . |
| 4,976,720 | 12/1990 | Machold et al. ................. 606/194 |
| 5,006,119 | 4/1991 | Acker et al. . |
| 5,032,113 | 7/1991 | Burns . |
| 5,035,705 | 7/1991 | Burns . |
| 5,037,404 | 8/1991 | Gold et al. . |
| 5,041,089 | 8/1991 | Mueller et al. ..................... 604/96 |
| 5,047,045 | 9/1991 | Arney et al. . |
| 5,061,257 | 10/1991 | Martinez et al. . |
| 5,078,727 | 1/1992 | Hannam et al. . |
| 5,100,381 | 3/1992 | Burns . |
| 5,101,682 | 4/1992 | Radisch, Jr. et al. . |
| 5,168,864 | 12/1992 | Shockey ......................... 128/4 |
| 5,176,660 | 1/1993 | Truckai . |
| 5,176,661 | 1/1993 | Evard et al. . |
| 5,178,158 | 1/1993 | de Toledo . |
| 5,199,950 | 4/1993 | Schmitt et al. ..................... 604/95 |
| 5,221,255 | 6/1993 | Mahurkar et al. ................... 604/43 |
| 5,246,430 | 9/1993 | MacFarlane ..................... 604/282 |
| 5,300,025 | 4/1994 | Wantink ......................... 604/96 |
| 5,308,342 | 5/1994 | Sepetka et al. ................... 604/282 |
| 5,314,409 | 5/1994 | Sarosiek et al. ................... 604/101 |
| 5,324,253 | 6/1994 | McRea et al. .................... 604/282 |

FOREIGN PATENT DOCUMENTS

| | | |
|---|---|---|
| 0279959A1 | 8/1988 | European Pat. Off. . |
| 0421650A1 | 4/1991 | European Pat. Off. . |
| 5253304 | 10/1993 | Japan ........................ 604/282 |
| WO92/07507 | 5/1992 | WIPO . |
| WO93/02733 | 2/1993 | WIPO . |
| WO93/20881 | 10/1993 | WIPO . |
| WO93/23107 | 11/1993 | WIPO . |

*Primary Examiner*—John D. Yasko
*Assistant Examiner*—Adam J. Cermak
*Attorney, Agent, or Firm*—Townsend and Townsend and Crew

[57] ABSTRACT

Multilumen catheters are provided with an axially decreasing stiffness by the incorporation of a hollow tube formed of a relatively stiff material into the catheter construction. The tube may either encircle the catheter as an external shell or reside inside one of the lumens as a liner. The stiffness variation may be attained by extending the hollow tube only part of the distance from the proximal to the distal ends of the catheter or by varying the construction of the hollow tube.

1 Claim, 3 Drawing Sheets

REINFORCED MULTILUMEN CATHETER FOR AXIALLY VARYING STIFFNESS

This invention relates to medical catheters designed for insertion into bodily cavities through long and convoluted passageways.

BACKGROUND OF THE INVENTION

Many medical procedures involve the insertion of catheters through bodily lumens such as blood vessels, nasal passages, urethral passages and the like to reach cavities or regions of the body where a therapeutic function is to be performed. Often, the lumens are convoluted or branched, particularly in the case of blood vessels, and insertion of the catheter so that its distal end reaches the desired location involves steering and maneuvering of the catheter through delicate, narrow passages, and the bending and curving of the catheter to conform to the shapes of the passages. This quality of the catheter is commonly referred to as "steerability." Many of the sites sought to be reached are also a considerable distance from the point of entry of the catheter into the body. Pushing the catheter shaft in far enough to reach these sites requires that the shaft be stiff enough so that it will not bend back over itself or form kinks. The term "pushability" has been used to characterize this quality. To accommodate these two needs, catheters have been constructed in different ways to achieve a proximal end which is stiffer than the distal end, and many of these constructions are complicated and expensive to manufacture.

Multilumen catheters offer even greater problems since they are of larger diameter than single-lumen catheters and require open space for the lumens. The open space reduces the amount of cross-sectional area and hence the opportunity for the incorporation of structural features to add to or vary the stiffness of the catheter shaft.

SUMMARY OF THE INVENTION

These and other needs are addressed by the present invention, which resides in multilumen catheter shafts with a stiffness that varies along the length of the shaft, thereby providing both pushability and steerability, and thus the capability of inserting the catheters through long bodily passages which terminate in convoluted, closely bent or curved, or intricately branched regions prior to or at the site of the region where the presence of the functional tip of the catheter is required. Axial variation in the stiffness of these catheter shafts is provided by the incorporation of a hollow tube into the construction of the shaft, the tube material having greater stiffness than the material of which the remainder of the catheter is constructed. The hollow tube may itself vary in stiffness, or it may extend less than the full length of the catheter shaft such that the tube imparts an increase in stiffness only to the proximal segment of the catheter which the tube occupies. For a tube which itself varies in stiffness, the variation can be achieved either by a variation in the material of construction used for the tube, or by the thickness of the tube. The variation can be stepwise, with two or more steps, or continuous, either in a linear or nonlinear manner. The axial variation in stiffness can also be achieved by the use of two or more tubes, all beginning at the proximal end but differing in length, again providing a stepwise variation in stiffness. In any of these various embodiments of the invention, the tube(s) may either form the exterior surface of the catheter shaft or form a lining in one or more of the lumens.

The use of a hollow tube or tubes in accordance with this invention offers the advantage of introducing a relatively stiff material of construction which may be unsuitable for use at the distal tip of the catheter, where greater flexibility is needed. The tube material will be sufficiently stiff that any increase in the catheter diameter when the tube surrounds the outer circumference of the catheter, or any decrease in the cross section of a lumen when the tube is a lining for the lumen, is small enough to have at most a minimal effect on the diameter of the catheter or the width of the lumen. Another advantage offered by the hollow tube is that it adds to the hoop strength of the catheter, lessening its tendency to expand or rupture due to a high pressure fluid inside one or more of the lumens.

The lumens of catheters in accordance with this invention remain available for use for a variety of functions, including accommodating guidewires, passing drugs and other fluids used for perfusion of the bodily cavity, draining fluid from the bodily cavity, or, in the case of balloon-tipped catheters, passing a pressurized inflation fluid to the distal end of the catheter to inflate the balloon.

Details of these and other features of the invention and preferred embodiments will be apparent from the description which follows.

DETAILED DESCRIPTION OF THE INVENTION AND PREFERRED EMBODIMENTS

While this invention is generic in scope, it will be best understood by a detailed discussion of specific embodiments.

Figure 1:
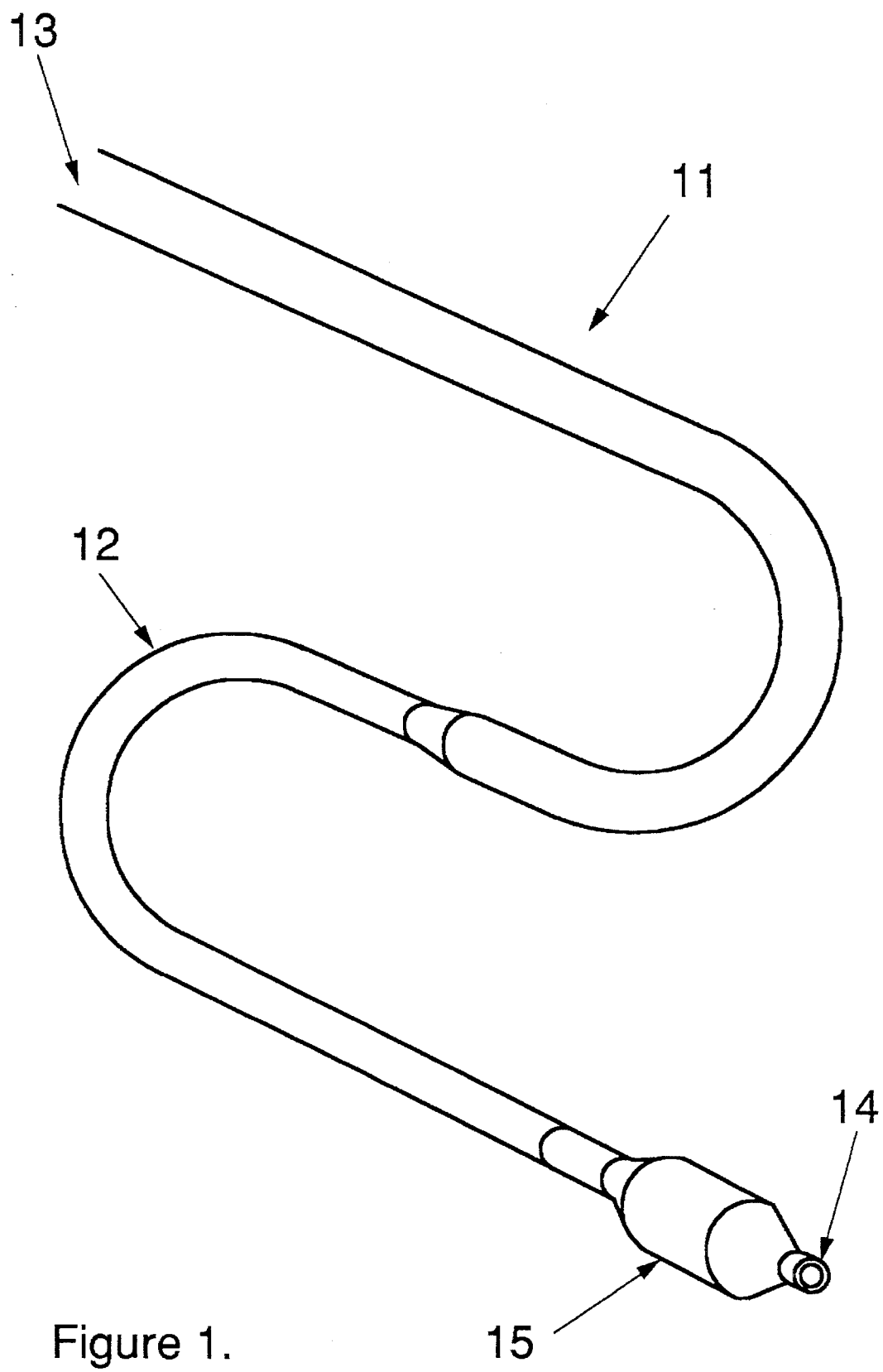
FIG. 1 is a depiction of a catheter which may incorporate the features of the present invention.

FIG. 1 depicts a catheter 11 in which the invention may be incorporated. This is one of many different types of catheters for a wide variety of uses, all of which can benefit from the present invention. The catheter depicted in FIG. 1 is a balloon angioplasty catheter for coronary angioplasty procedures. The catheter includes an elongated shaft 12 with proximal 13 and distal 14 ends, and a dilatation balloon 15 at the distal end. Any of a wide variety of other functional elements may be substituted for the balloon, or incorporated in addition to it. Furthermore, additional fixtures and connections not shown in the drawing will be included at the proximal end 13 to serve as fluid connections and to facilitate manipulation of the catheter, positioning of the distal end, inflation and deflation of the balloon 15, and/or activation of any additional functional elements at the distal end (not shown). In accordance with the invention, the shaft 12 varies in stiffness along its length, with the proximal end 13 regions exhibiting a relatively high stiffness, which decreases either gradually or in stepwise manner toward the distal end 14.

Figure 2:
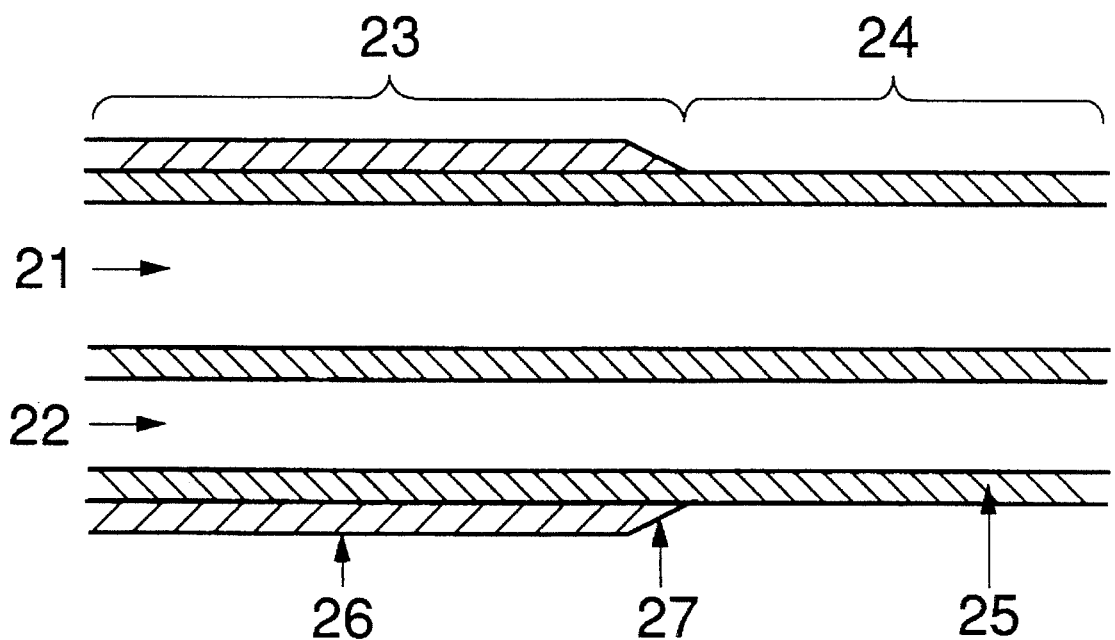
FIG. 2 is a longitudinal cross section of a segment of a catheter like that of FIG. 1, illustrating one embodiment of the invention.

An enlarged longitudinal cross section of a segment of the catheter is shown in FIG. 2. The catheter is shown to have two lumens 21, 22, both extending the full axial length of the catheter shaft. Catheters within the invention may also contain three or more lumens. Also, the lumens in the catheter shown in FIG. 2 are neither coaxial with the catheter axis nor with each other. The invention also extends to multilumen catheters in which one or more of the lumens are annular in shape.

The segment shown in the drawing is in the region where a transition in stiffness occurs from a proximal region of relatively high stiffness 23 to a distal region of lesser stiffness 24. While the shaft body itself 25 extends the full length of the shaft, the proximal region 23 is made stiffer by the hollow tube 26 of denser and stiffer material which encircles the shaft body and terminates at the transition point between the two regions. The distal terminus 27 of the hollow tube is tapered to form a smooth transition. A transverse cross section of the high stiffness region 23 of the shaft is shown in FIG. 3.

Figure 4:
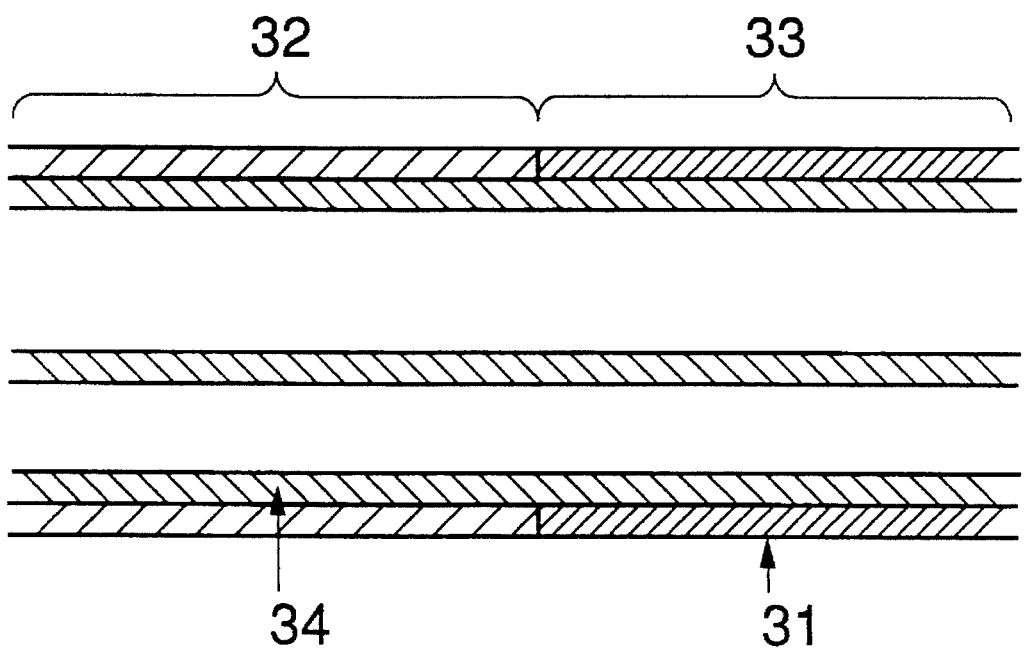
FIG. 4 is a longitudinal cross section of a segment of another catheter like that of FIG. 1, illustrating a second embodiment of the invention.

An alternative means of achieving proximal and distal regions of differing stiffness is shown in FIG. 4. In this construction, the hollow tube 31 extends the full length of the shaft, but the tube itself is in two segments, a proximal segment 32 and a distal segment 33. The variation in stiffness is achieved by a variation in the material of construction between these two segments, or the manner in which the material is extruded or treated in forming the two segments. In either case, all parts of the hollow tube are of the same wall thickness and are stiffer than the interior portion 34 constituting the remainder of the shaft material.

Figure 5:
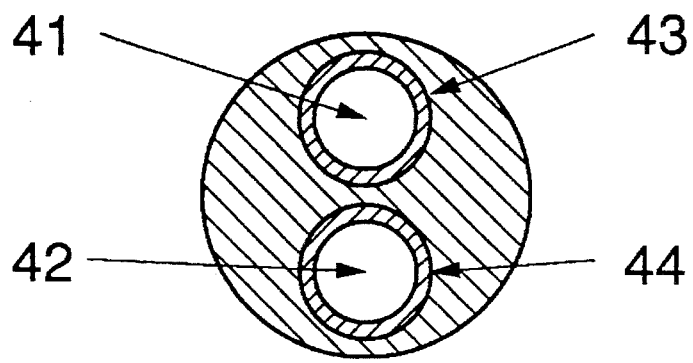
FIG. 5 is a transverse cross section of still another catheter, illustrating a third embodiment of the invention.
Figure 6:
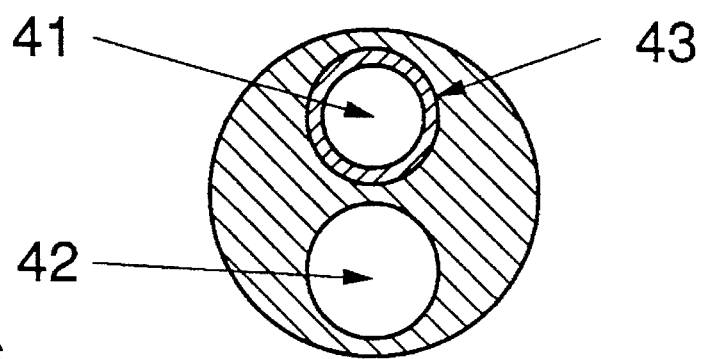
FIG. 6 is a transverse cross section of the catheter of FIG. 5, taken at a different axial location along the catheter.

FIGS. 5 and 6 depict a third means of achieving proximal and distal regions of differing stiffness in the catheter shaft. These two drawings represent transverse cross sections of the catheter shaft at two different locations along the shaft axis, FIG. 5 representing a location in the proximal region where the greater stiffness is required, and FIG. 6 representing a location in an intermediate region where the stiffness is intermediate between that of the proximal and distal regions.

Figure 3:
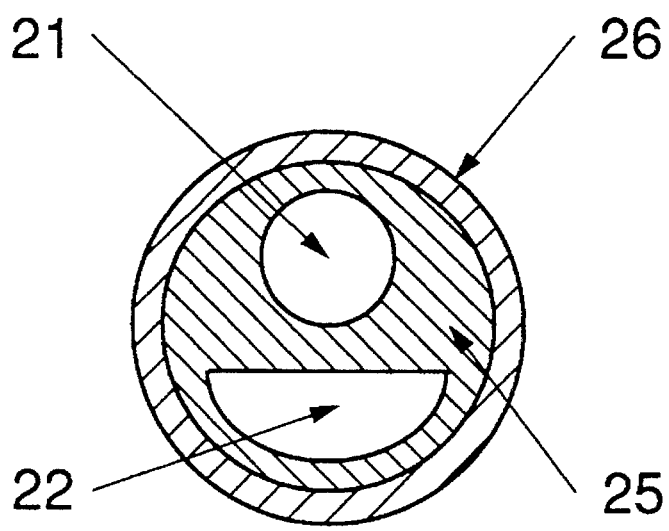
FIG. 3 is a transverse cross section of the catheter whose longitudinal cross section is shown in FIG. 2.

The construction shown in FIGS. 5 and 6 differs from those of FIGS. 2 and 3 in several ways. First, while the catheter contains two lumens 41, 42, both lumens in this construction are of circular cross section. Second, there are two hollow tubes 43, 44 rather than just one, one of the tubes 43 being longer than the other and extending into the intermediate region while the other 44 terminates at the distal end of the proximal region. The longer hollow tube 43 terminates at the distal terminus of the intermediate region and does not extend into the distal region. Third, both hollow tubes 43, 44 reside inside the lumens rather than encircling the entire catheter shaft. Each hollow tube is of a constant wall thickness and stiffness, and the variation in stiffness of the catheter shaft is in two stages, the two tubes a cumulative stiffening effect in the proximal region, the single tube being the sole stiffening element in the intermediate region, and the absence of such tubes in the distal region leaving that region the least stiff of the three.

As a further alternative, FIGS. 5 and 6 may represent two independent catheters (rather than cross sections at two different axial locations on a single catheter). According to this alternative, only one lumen in the catheter of FIG. 6 contains the reinforcing hollow tube while both lumens in the catheter of FIG. 5 contain reinforcing hollow tubes.

Although not shown in the drawings, a still further means of achieving a decrease in stiffness along the length of the shaft is by narrowing the wall thickness of the hollow tube toward the distal end of the shaft. This may be done stepwise or in a continuous manner.

The dimensions of the catheter, its shaft, the lumens and the hollow tube are not critical and may vary widely depending on the functions which the catheter is designed to serve and the particular type or configuration of bodily vessel or cavity which the catheter is to be used in. The length of the catheter, for example, will be within typical ranges of catheters as they are currently in use in medical procedures or have been disclosed in the literature. For catheters intended to be used in a patient's vasculature, the length of the catheter shaft will most often be at least about 100 cm, and preferably at least about 120 cm. The outer diameter of the catheter shaft in most cases will be from about 0.01 inch (0.0254 cm) to about 0.1 inch (0.254 cm). Typical balloon angioplasty catheters are approximately 135 cm in length, including the balloon, and an outer diameter of approximately 0.04 inch (0.102 cm). For hollow tubes which do not extend the full length of the shaft, the distal terminus of the hollow tube will most often be at least about 20 cm from the distal end of the shaft, and preferably at least about 30 cm from the distal end of the shaft. The wall thickness of a hollow tube will most often be within the range of about 0.001 inch (0.00254 cm) to about 0.01 inch (0.0254 cm). It is presently contemplated that for catheter shafts of approximately 135 cm in length and an outer diameter of about 0.04 inch (0.102 cm), a typical hollow tube will have a length of about 100 to about 110 cm and a wall thickness of about 0.002 to about 0.003 inch (0.0051 to 0.0076 cm).

The materials of construction may vary widely, the primary criteria being the stiffness range and the difference in stiffness between the shaft material and the hollow tube material. Prime examples of materials for the shaft are polyethylene and polyurethane, although any readily formable or extrudable material from which a shaft with dimensions and lumens of the requisite precision can be made may be used. Examples of materials of construction for the hollow tube are polyimide, hypotube (a stainless steel containing nickel and titanium as alloying components), polytetrafluoroethylene and related materials known as TEFLON, high density polyethylene, and composites of these materials.

The hollow tube can be secured to the catheter shaft by any of a variety of methods. Examples are lamination, co-extrusion, dip coating, adhesive bonding, and a tolerance fit. Methods of effecting these techniques are well known in the art.

The foregoing is offered primarily for purposes of illustration. It will be readily apparent to those skilled in the art that the materials, dimensions, configurations and other parameters of the catheter may be further modified or substituted in various ways without departing from the spirit and scope of the invention.

What is claimed is:

1. A multilumen medical catheter for insertion into a body cavity through elongated and convoluted narrow passageways in the body, said medical catheter comprising:

a shaft having proximal and distal ends;

a functional element at said distal end of said shaft;

a plurality of lumens extending axially through said shaft;

first and second hollow tubes of material substantially more rigid than said shaft and affixed thereto, said hollow tubes extending from said proximal end of said shaft to differing distances toward said distal end, thereby cumulatively imparting to said shaft a stiffness varying in stepwise manner, progressing from a maximum stiffness at the proximal end of said shaft top a minimum stiffness at the distal end of said shaft, said first hollow tube being disposed inside one of said lumens and said second hollow tube being disposed inside another of said lumens.

* * * * *